United States Patent [19]

Backman

[11] Patent Number: 4,839,286
[45] Date of Patent: Jun. 13, 1989

[54] METHOD OF BIOSYNTHESIS AND CELLS THEREFOR

[75] Inventor: Keith C. Backman, Bedford, Mass.

[73] Assignees: Biotechnica International, Inc., Cambridge, Mass.; H. J. Heinz Company, Pittsburgh, Pa.

[21] Appl. No.: 653,193

[22] Filed: Sep. 24, 1984

Related U.S. Application Data

[63] Continuation-in-part of Ser. No. 540,190, Oct. 7, 1983, abandoned.

[51] Int. Cl.$^4$ .................. C12P 13/22; C12N 1/20; C12N 15/00; C12R 1/19
[52] U.S. Cl. .................. 435/108; 435/252.33; 435/320; 435/172.3; 435/849; 935/29; 935/41; 935/60; 935/73
[58] Field of Search .................. 435/108, 172.3, 253, 435/317, 232; 935/14, 27, 29, 41, 60, 73

[56] References Cited

U.S. PATENT DOCUMENTS

| | | | |
|---|---|---|---|
| 4,278,765 | 7/1981 | Debabov et al. | 435/172.3 |
| 4,374,927 | 2/1983 | Sninsky | 435/68 |
| 4,681,852 | 7/1987 | Tribe | 435/108 |

FOREIGN PATENT DOCUMENTS

| | | | |
|---|---|---|---|
| 72727/81 | 9/1982 | Australia. | |
| 0077196 | 4/1983 | European Pat. Off. | 435/172.3 |
| 0126338 | 11/1984 | European Pat. Off. | |
| 0190921 | 8/1986 | European Pat. Off. | 435/172.3 |

OTHER PUBLICATIONS

Roberts, T. et al., *Proc. Natl. Acad. Sci.*, vol. 76, No. 2, pp. 760–764, 1979.
Gowrishankar, J. et al, *J. Bacteriol*, vol. 150, No. 3, pp. 1130–1137, 1982.
Yanofsky, C., *Nature*, vo. 289, pp. 751–758, 1981.
Sugimoto, S., et al, *App. Microbiol. Biotechnol*, vol. 22, pp. 336–342, 1985.
Stryer, *Biochemistry*, 2 ed. pp. 675–678 (Freeman and Co. San Francisco 1981).
Bernhard et al. (1979), Gene 5:59–76, U.S. Ser. No. 527,490, filed 8/29/83, by Modrich et al.
Remaut et al. (1981), Gene 15:81–93.
Franklin (1971), pp. 621–638, *The Bacteriophage Lambda;* Cold Spring Harbor Laboratory, Cold Spring Harbor, NY (Hershey Ed.).
Zurawski, G. et al, *Proc. Natl. Acad. Sci.*, vol. 75, No. 10, pp. 4271–4275, 1978.
Chemical Abstracts (1982), vol. 97:180140e (Japanese Appl. 80/154,706).
Davison et al. (9174), Mol. Gen. Genet. 130:9–20.
Sprinson et al. (1976), Acta. Microbiol. Acad. Sci. Hung. 23:167–170.
Rood et al. (1980) J. Bacteriology 144:552.
Liu et al., (1983), J. Biol. Chem. 258:7469–7475.
DeBoer et al. (1982), PNAS USA 80:21–25.
Jacob et al. (1965), J. of Molecular Biology 31:704–719.
Casadaban et al. (1979), Proc. Nat'l. Acad. Sci., USA 76:(9):4530–4533.
Backman et al., (1976), Proc. Nat'l. Acad. Sci. USA 73:4174.

*Primary Examiner*—Jayme A. Huleatt

[57] ABSTRACT

An expression vector having two structural genes that form a synthetic operon expressed under the control of a single regulatory sequence. The operon genes correspond to the structural component of naturally occurring genes whose expression is controlled by distinct separate regulatory sequences. The operon genes code for enzymes in a biosynthetic pathway for producing a desired compound, and at least one of those operon genes is feedback derepressed. The vector is used to transform host cells that are cultured to produce the desired product.

10 Claims, 4 Drawing Sheets

METHOD OF BIOSYNTHESIS AND CELLS THEREFOR

BACKGROUND OF THE INVENTION

This application is a continuation-in-part of my copending application U.S. Ser. No. 540,190 filed Oct. 7, 1983, now abandoned.

This invention relates to the in vivo production of desired compounds.

A fundamental limitation of in vivo methods of producing compounds is that organisms often have regulatory mechanisms to limit synthesis to amounts sufficient for the organism's own needs, thus avoiding waste of the organism's raw materials and energy. Often regulation of biosynthesis is effected at the level of gene expression. For example, sufficiency or surfeit of a particular compound causes a cessation in the synthesis of one or more of the enzymes that catalyze reactions in the biosynthetic pathway of that compound. Genetic sequences, located in the vicinity of the structural gene coding for the enzyme, regulate expression of the enzyme. In some cases, more than one kind of regulatory sequence may be associated with a gene. Examples of such regulatory sequences include: promoters, operators, attenuators, antiterminators, ribosome binding sites, and sites for positive effectors.

Bernard et al., [1979] Gene 5:59–76 and Remaut et al. [1981] Gene 15:81–93 disclose inserting restriction fragments containing Salmonella genes for enzymes in the tryptophan-synthesis pathway into vectors downstream from the phage $p_L$ promoter. Expression of the genes is obtained under control of $p_L$. Bernard specifically involves the trp operon genes. Bernard also says that it should be possible to insert a promoterless DNA fragment carrying a gene specifying a measurable enzyme into an EcoRI site in the above-described expression vectors. Remaut involves genes for tryptophan synthetase A.

Franklin, (1971) pp. 621–638, *The Bacteriophage Lambda;* Cold Spring Harbor Laboratory, Cold Spring Harbor, N.Y. (Hershey Ed.) and Davison et al. (1974) Mol. Gen. Genet. 130:9–20 disclose transcription of the tryptophan operon either from the $p_L$ promoter of phage lambda or from its naturally occurring promoter.

Stryer, *Biochemistry,* 2 ed. pp. 675–678 (Freeman and Co. San Francisco 1981) discloses that expression of the naturally occurring tryptophan operon of *E. coli* including trpA and trpB is subject to operator corepression by a complex of tryptophan and the trpR gene product. Expression of that operon is also regulated by a leader peptide attenuation control that depends on the availability of tryptophan for leader peptide synthesis.

Tribe, Australian Application 72727/81, discloses a strain of *E. coli* mutants which have been mutated to produce higher levels of chorismate mutase-prephenate dehydratase (CMPD) and 3-deoxy-D-arabino-heptulosonate-7-phosphate (DAHP) synthase than are found in strains with wild-type regulation of those enzymes.

Sninsky et al., U.S. Pat. No. 4,374,927, discloses fusing the lac promoter-operator to the structural gene for chloramphenicol acetyltransferase. Expression of that structural gene is regulated by a repressor whose activity is temperature related.

Chemical Abstracts (1982) Vol. 97:180140e (Japanese Appl. 80/154,706), discloses a strain of *E. coli* containing a trp operon that is resistant to feedback inhibition by a repressor.

Sprinson et al., (1976) Acta. Microbiol. Acad. Sci. Hung. 23:167–170, discloses Salmonella mutants that are resistant to phenylalanine analogs, and which exhibit coordinate derepression of DAHP synthetase (tyr) and prephenate dehydrogenase (aro).

Modrich et al., U.S. Ser. No. 527,490 filed Aug. 29, 1983, now abandoned, discloses placing genes for EcoRI endonuclease and methylase downstream from a lambda promoter so as to be expressed by that promoter and thereby take advantage of the control afforded by the lambda repressor. The behavior of these *E. coli* genes in the reported construction indicated that they may include a naturally occurring internal promoter.

Rood et al., (1980) J. Bacteriology 144:552, discloses certain plasmids designed for overproduction of enzymes coded for by the tyrosine operon in that the regulatory region of the operon on these plasmids has been altered so that it is not subject to the control of a specific repressor. The authors report that such plasmids give rise to modifications by insertions or deletions that decrease the level of expression of the tyrosine operon.

Liu et al., (1983) J. Biol. Chem. 258:7469–7475, discloses placing the gene coding for guanine-xanthine phosphoribosyltransferase under the control of the lambda phage leftward promoter.

DeBoer et al., (1982) PNAS U.S.A. 80:21–25, discloses expression of the enzyme galactokinase under the influence of a hybrid promoter generated from the lac and trp promoters. The hybrid promoter can be repressed by the lac repressor.

Jacob et al., (1965) J. of Molecular Biology 31:704–719 discloses isolation of a mutant having a genetic deletion which results in fusion of a part of the lac operon to a part of the pur operon, forming a new operon which is subject to repressive regulation by purines.

Casadaban et al., (1979) Proc Nat'l Acad. Sci. U.S.A. 76 (9):4530–4533 discloses techniques to fuse the lactose operon (lac) structural genes minus the lac promoter, to non-lac operon promoters, so that the lac operon is expressed under the control of a non-lac operon promoter.

Backman et al., (1976) Proc. Nat'l Acad. Sci. U.S.A. 73:4174 discloses construction of a plasmid in which the promoter of the lac operon is placed adjacent the repressor gene (cI) of bacteriophage λ, by recombinant techniques. Synthesis of the λ repressor is thus regulated by the lac operator and promoter. By supplying an excess of lac operator sites in comparison to the available lac repressor, synthesis of λ repressor is increased.

SUMMARY OF THE INVENTION

In one aspect, the invention features an expression vector for transforming cells to produce a desired compound by a biosynthetic pathway. The vector includes at least two structural genes that are a synthetic operon, meaning that, on the vector construction, they are expressed under the control of a single regulatory sequence and promoter, whereas in naturally occurring constructions, genes corresponding to the operon genes are expressed under the control of distinct separate regulatory sequences. The operon genes code respectively for enzymes in the biosynthetic pathway, and at least one of those genes is feedback derepressed. The natural gene corresponding to at least one of the operon genes is feedback repressed. By feedback repressed, I mean that expression of the natural gene is subject to repression by a control substance that is a pathway intermediate or product. The corresponding operon gene is derepressed, meaning that the vector promoter is foreign to the repressed natural gene and expresses operon genes without repression from the pathway intermediates or product. By foreign I mean that the promoter does not naturally occur in position to initiate transcription of the corresponding natural gene. Thus, the vector enables uninhibited expression of the operon genes in the presence of all biosynthesis pathway intermediates as well as the pathway product.

In preferred embodiments of the first aspect, the derepressed gene product catalyzes a rate-limiting reaction in the biosynthesis pathway. Expression of the naturally occurring gene that corresponds to the derepressed operon gene is subject to dual regulatory mechanisms: (1) leader/attenuator repression in which the naturally occurring regulatory DNA codes for a leader peptide that alters the structure of an attenuator site on the regulatory DNA transcript to inhibit expression of the structural gene, the rate of synthesis of the leader peptide being dependent on the availability of a pathway intermediate or product; and (2) operator/repressor repression in which a pathway intermediate or product interacts with a repressor protein, causing it to bind to an operator site on the naturally occurring regulatory DNA to prevent transcription of the structural gene. The feedback control substance is the same for both types of natural regulation of the corresponding derepressed gene and is the amino-acid produce of the pathway, e.g. L-phenylalanine. The vector promoter is most preferably the lac promoter, the aroF promoter, or the tet promoter of pBR322. Other preferred promoters include the aroH promoter and the phage M13 gene II promoter. The operon genes include pheA and aroF or aroH.

In a second aspect, the invention features an expression vector for producing phenylalanine in a host cell; the vector has a synthetic construction that includes a pheA structural gene and a regulatory sequence that is foreign with respect to the pheA structural gene and is effective in the host cell to express the pheA gene in the presence of phenylalanine synthesis pathway intermediates and products.

In preferred embodiments of the second aspect, the pheA gene is derived from a naturally occurring pheA gene by removing the naturally occurring regulatory sequence from the structural gene. The preferred regulatory sequences are those described above for the first aspect.

In other aspects, the invention features a host cell engineered with one of the above vectors and a method of making the desired compound by growing the cell in a culture medium and recovering the product from that medium.

In preferred embodiments of the other aspects, the cells are *E. coli*, and the desired compound is phenylalanine.

The invention enables production of compounds by the above-described engineered cells, which avoid normal synthesis-inhibiting regulatory mechanisms, and therefore do not curtail synthesis in response to elevated levels of the product. In many applications, as the product builds up, it is released to the supernatant milieu, thus making recovery of the biochemical more convenient.

The engineered vector is able to override natural regulatory modes, e.g., leader/attenuator regulation and operator/repressor regulation. Specifically, exogenous regulatory DNA can effectively control gene expression of gene products that are key enzymes in the pathway, and this finding has broad applicability to other promoters such as phage m13 gene II promoter and the tet promoter of pBR322. Finally, the inclusion of several pathway genes in the same synthetic operon is efficient, simplifies transformation, and reduces the total number of genetic elements necessary, thus reducing the complexity of the genome in the engineered organism.

These factors support a higher level of gene expression, and thereby increase the rate of the rate-limiting step in the pathway, as well as the rate of other pathway steps catalyzed by operon gene products.

Other features and advantages of the invention will be apparent from the following description of the preferred embodiments thereof and from the claims.

DESCRIPTION OF THE PREFERRED EMBODIMENTS

Figure 1:
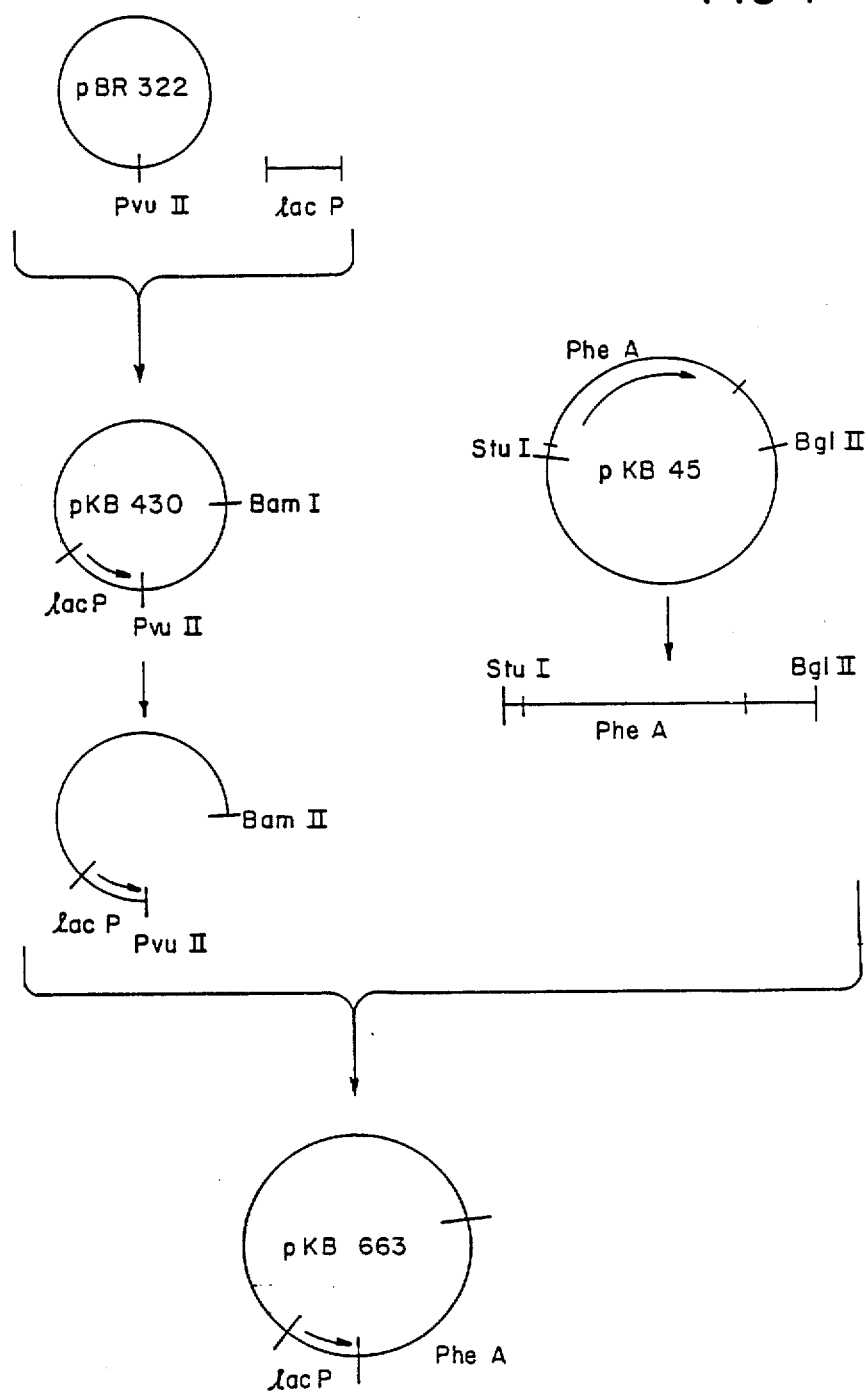

I first briefly describe the drawings.

DRAWINGS

FIGS. 1-4 are diagrams representing respectively steps in the engineering of plasmids pKB663, pKB712, pKB750, and pKB766.

EXPRESSION VECTORS

The desired product compound is synthesized by cells via a synthesis pathway with steps that are targets of gene-expression regulation. That is, regulation at a step in the synthesis pathway is accomplished by varying the level of expression of the gene for an enzyme to vary the amount of enzyme in the cell, and such regulation involves DNA sequences adjacent to the regulated gene.

Replacement of such regulatory DNA sequences with heterologous regulatory sequences, by recombinant DNA techniques, is used to circumvent the normal regulation of a biosynthetic pathway and augment the production of a biochemical beyond the point where normal regulation would have halted its further production.

The pathway steps selected for derepression should be rate-limiting ones so that successful derepression will show a gain in product yield. The dual-mechanism-repressed enzymes are the specific targets. In order to deactivate both of the repression mechanisms, it is preferable to remove the regulatory DNA that naturally occurs with the structural gene whose expression is being derepressed and to add a foreign promoter (i.e. one that in naturally occurring structures does not govern expression of the gene).

In the preferred embodiments comprising a synthetic operon, the promoter may be foreign to both of the genes, or it may be foreign only to the gene selected for derepression. The two synthetic operon genes should be close to each other, but there may be short, or even quite long, sequences between them, as long as there are no signals to stop transcription between the genes. Each synthetic operon gene corresponds to the structural component of a naturally occurring gene. By the term "corresponds to," I mean that the operon gene is either identical or sufficiently related to the naturally occurring structural gene that the operon gene codes for an enzyme that catalyzes the reaction catalyzed by the natural gene product.

Choice of the other operon component offers an opportunity to engineer a construction that highly expresses another pathway enzyme. One preferred choice is another rate-critical pathway step. The other operon component also may be selected to simplify the cloning procedure by selecting a gene with regulatory material that is used on the vector. In that case, the 3' end of the operon may be the derepressed structural gene, and the 5' end may be the other member of the operon with its naturally occurring regulatory sequence.

If a promoter is used that is exogenous or foreign to both members of the operon, the members can be linked in either order. Additional structural genes may be added to the operon, and more than one of them may be feedback repressed in its naturally occurring structure, so that it also is derepressed by insertion in the operon.

The following three examples of preferred vectors pKB663, pKB712, and pKB750 are illustrative.

Each vector is useful in synthesizing the amino acid L-phenylalanine by derepressing expression of the pheA gene of *E. coli*, which is naturally regulated in response to available phenylalanine. The product of pheA, the dual-function enzyme chorismate mutase-prephenate dehydratase, effects the penultimate steps in phenylalanine biosynthesis. Regulation of pheA expression occurs both by a repressor/operator system and by a leader peptide/attenuator system. When sufficient or excess phenylalanine is available, expression of pheA is turned off, and phenylalanine synthesis stops.

The DNA for the pheA-associated promoter/operator and leader peptide/attenuator is replaced with DNA from another promoter. Cells harboring such a construct do not halt expression of pheA nor stop phenylalanine biosynthesis in response to elevated phenylalanine. In consequence, such cells release phenylalanine into the supernatant milieu.

Construction of pKB663

One expression vector for producing phenylalanine is illustrated in FIG. 1. A fragment of DNA carrying the pheA gene of *E. coli* but not its associated promoter, operator, leader peptide, or attenuator, is prepared from plasmid pKB45 (Zurawski et al. Proceedings of the National Academy of Sciences 75:4271–4274 [1978]) by digestion with endonucleases StuI and BglII. The next step involves plasmid pKB430, which is a derivative of pBR322 that carries a 95 bp AluI generated DNA fragment containing the lactose operon promoter-operator cloned in the endonuclease PvuII cleavage site of pBR322 such that a new PvuII site is created at the border of the lac promoter and the pBR322 sequences, and lac transcription proceeds across this PvuII site toward the tet region. The pheA-containing DNA fragment is cloned by standard techniques (Bolivar, F. and Backman, K. Methods in Enzymology, Vol. 68 [1980]) in pKB430 between the PvuII and BamHI cleavage sites, yielding pKB663. In addition to the pheA gene, pKB663 also carries a gene which determines resistance to β-lactam antibiotics.

Construction of pKB712

Figure 2:
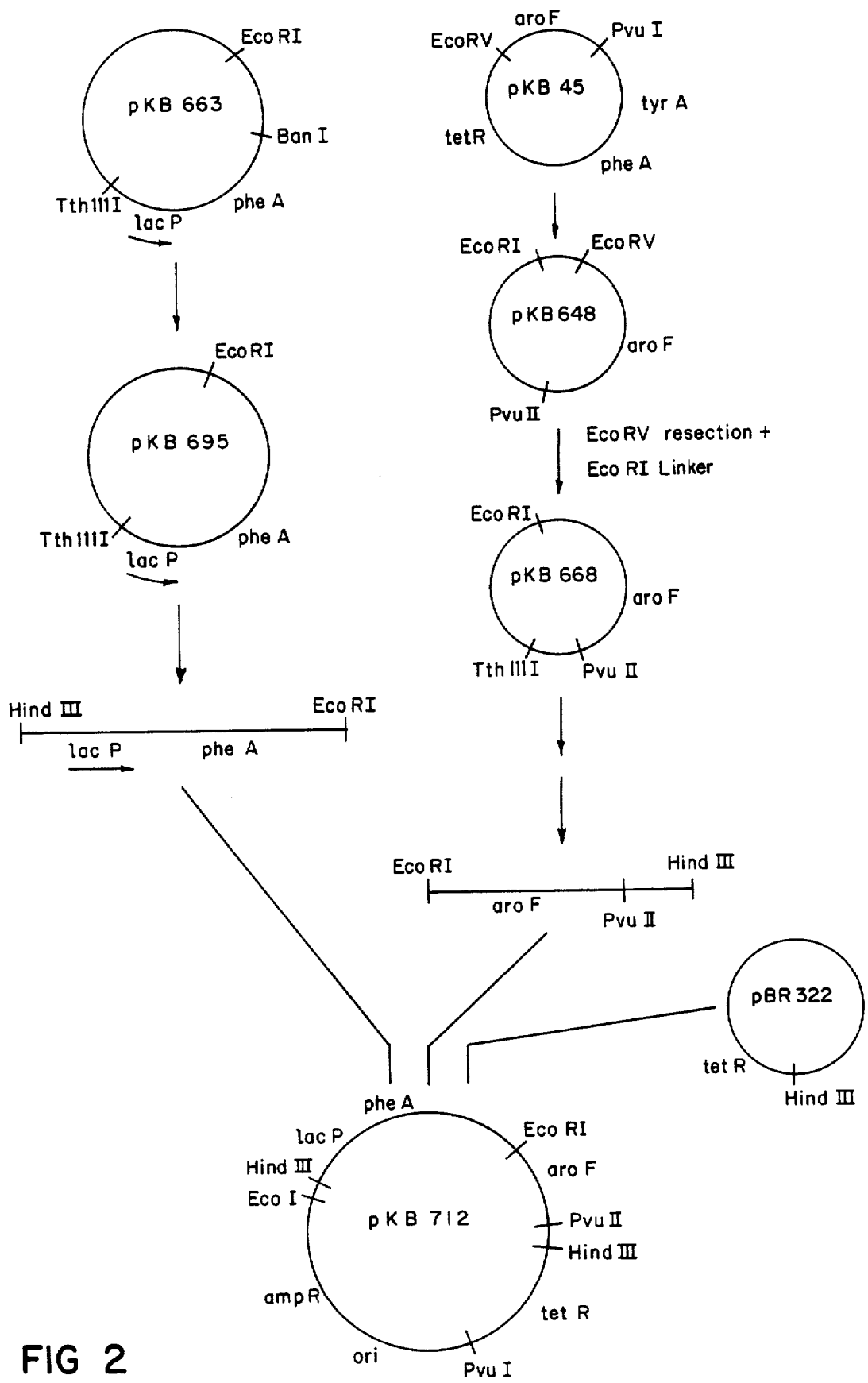

FIG. 2 depicts the construction of pKB712 from two components:

The first component is the lac operon-pheA fusion described above with respect to pKB663. The BanI site just past the end of the pheA gene is converted to an EcoRI site by abutting to a filled in EcoRI site. Specifically, pKB663 is treated by inserting a HindIII linker at TthlllI site 5' to the lac promoter.

The second component is the aroF structural gene; specifically aroF, contained on pKB45 is subcloned into pBR322 as an EcoRV to PvuII fragment, yielding pKB648. The aroF gene is preceded (5') by a EcoRV site which is cleaved and exonucleolytically resected, followed by insertion of an EcoRI linker positioned about 20-bp upstream from the aroF gene's ribosome binding site. Near the 3' end of aroF is a PvuII site which can be joined to the PvuII site of pBR322. The TthlllI site 3' to the gene thus cloned is changed to a HindIII by a linker.

The above two components are joined at their EcoRI ends and cloned in the HindIII site of pBR322.

In the pKB712, the two structural genes are joined at a point approximately eight nucleotides after the first stop codon at the end of pheA and approximately 20 nucleotides upstream from the ribosome binding site of the aroF gene.

Figure 3:
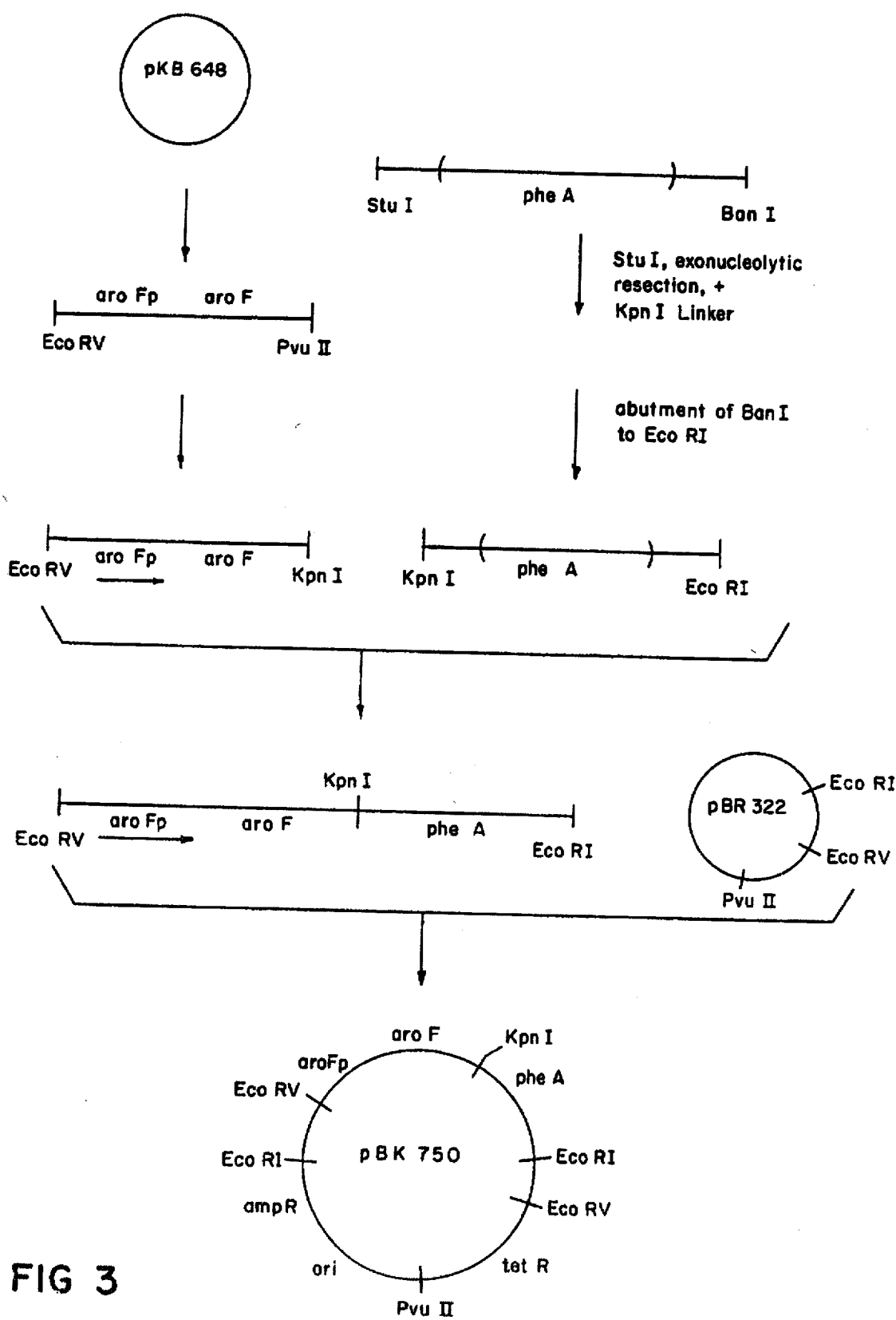

Construction of pKB750 pKB750 differs from all of the above-described expression vectors in that it is expressed under the control of the aroF promoter, not the lac promoter.

pKB750 is constructed as shown in FIG. 3 from two fragments.

The first fragment is an aroF gene with its naturally associated promoter, obtained by from pKB45 via pKB648; the segment begins with an EcoRV site 5' to the gene and ends with a KpnI site positioned next to the PvuII site at the end of aroF.

The second fragment is a pheA gene bounded by a KpnI site 5' to the gene and an EcoRI site 3' to the gene. The KpnI site is created by cleavage at the StuI side 5' to pheA (e.g. on pKB45 or a suitable derivative) and exonucleolytic resection towards pheA; KpnI linkers are then added. The EcoRI site is created by abutting a BanI site to a filled in EcoRI site.

These fragments are joined at their KpnI sites and cloned into pBR322.

Construction of pKB766

The pheA gene, or a synthetic operon that includes pheA, can be expressed from any of a number of exogenous promoters that are not regulated by pheA synthesis pathway compounds.

Figure 4:
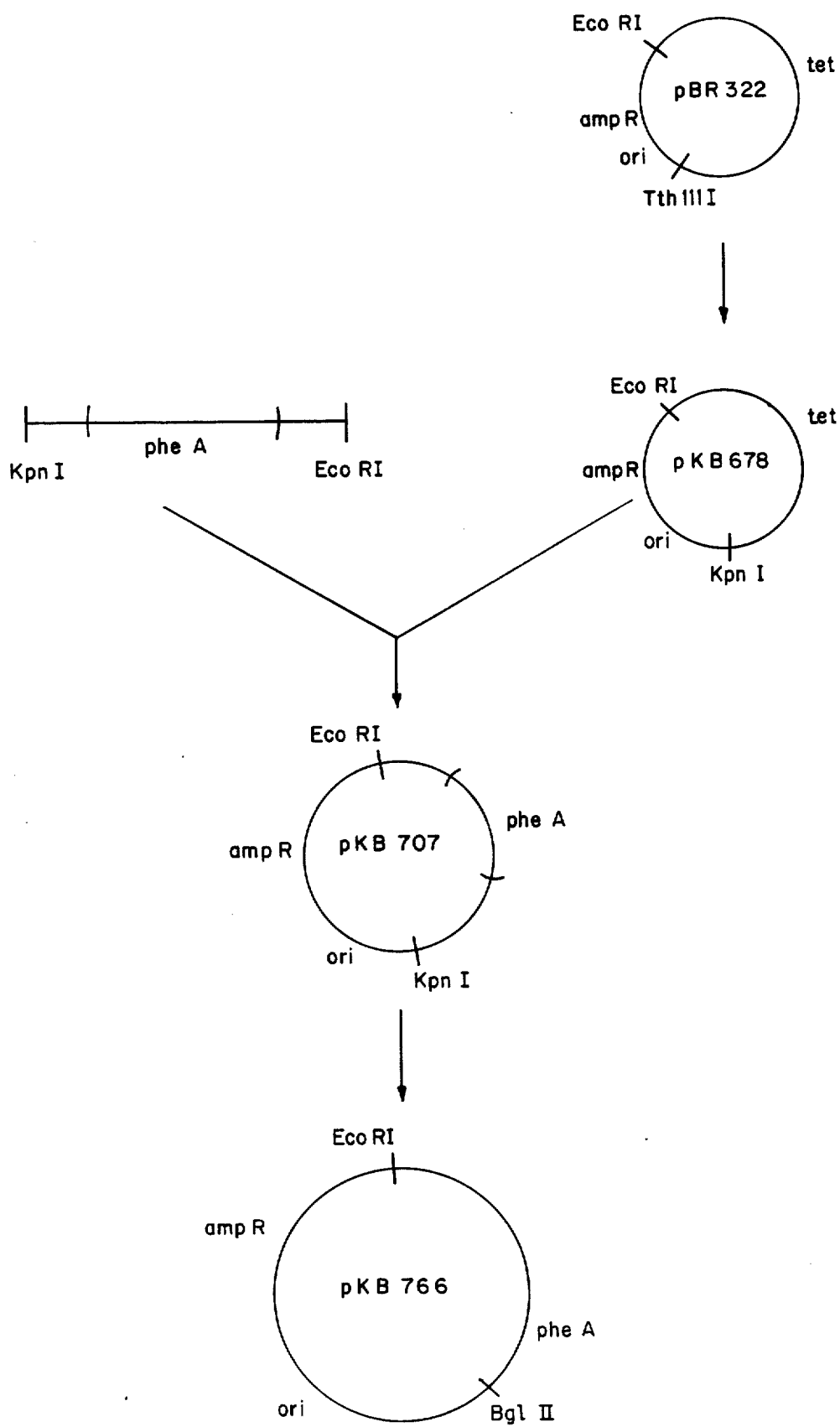

Suitable multipurpose cloning vehicles for making those constructions are pKB707 or pKB766, illustrated in FIG. 4.

pKB766 is constructed starting with the KpnI-EcoRI pheA-containing fragment illustrated in FIG. 3 cloned in vector pKB678 to yield pKB707. The KpnI site of pKB707 is readily converted to a BglII site by means of a linker yielding pKB766. pKB707 and pKB766 contain unique cloning sites 5' to the pheA gene. Insertion of any number of promoter-carrying DNA fragments in the KpnI site of pKB707 or the BglII site of pKB766 results in the synthesis of chorismate mutase-prephenate dehydratase in a manner unregulated by phenylalanine. For example, the gene II promoter from bacteriophage m13 and each of two promoters from the tet region of pBR322 [between the EcoRI site at position 1 and the BanI site at position 76] are each cloned onto DNA fragments having sticky ends compatible with BglII sticky ends and are then cloned into the BglII site of pKB766. *E. coli* are transformed and cultured as described below. Phenylalanine production is scored by ability to crossfeed a phenylalanine auxotroph. Although strains carrying pKB766 cannot crossfeed phenylalanine auxotrophs, all derivatives of pKB766 which carried a promoter were able to produce and secrete phenylalanine and thereby crossfeed a phenylalanine auxotroph. Thus, the promoter-carrying fragments are responsible for the observed phenylalanine secretion.

Production of Phenylalanine

*E. coli* K12 strain YMC9, which has been deposited with the American Type Culture Collection and has an accession number ATCC 33927 (Backman et al., Proceedings of the National Academy of Sciences U.S.A. 78 [1981], 3743-3747), is transformed with pKB663, yielding YMC9/pKB663. Plasmid pKB663 is available from strain YMC9/pKB663, which has been deposited with the American Type Culture Collection and has an accession number ATCC 39462. YMC9/pKB663 is cultured at 37° C. in M9 salts plus 4 mg/ml sodium acetate and 1 μg/ml thiamine, and culture turbidity is monitored using a Klett-Summerson Colorimeter (green filter). During growth of this strain on acetate, no detectable phenylalanine appears in the supernatant. When the culture density reaches either 45 or 148 Klett units, the cells are collected by filtration, resuspended in an equal volume of fresh medium, and glucose is added (final concentration: 4 mg/ml). Incubation is continued for 10 to 15 hours, at which point phenylalanine content in the supernatant is determined.

Alternatively, pKB663 is used to transform derivatives of YMC9 designated KB285 and KB280 which are described in my co-pending application, hereby incorporated by reference, entitled Cell Lines and Methods for Fermentation, U.S. Ser. No. 539,981 filed Oct. 7, 1983, now abandoned in favor of currently pending continuation-in-part application U.S. Ser. No. 860,543, filed May 7, 1986. KB280 and KB285 are deposited with the American Type Culture Collection with accession numbers ATCC 39461 and ATCC 39463, respectively. KB285/pKB663 or KB285/pKB663 may be used to synthesize L-phenylalanine as described in that application.

Phenylalanine concentration is determined microbiologically using phenylalanine assay medium (Difco) and *Pediococcus acidilactici* ATCC 8042 (Difco Manual, 1953).

As described above for pKB633, pKB712 and pKB750 can be used to transform a host such as *E. coli* YMC9 or derivatives thereof to yield a strain that secretes phenylalanine into the supernatant milieu.

Expression of pheA is directed by the foreign promoter, and production of phenylalanine is enhanced when the pheA structural gene is introduced as part of a synthetic operon, rather than as a single deregulated structural gene.

Vectors pKB663, pKB712, pKB750, and pKB766 have been deposited with the American Type Culture Collection in Rockville, Md. and are designated by accession numbers 39,462, 39,856, 39,857, and 39,858, respectively. Applicant's assignee, BioTechnica International, Inc. acknowledges its responsibility to replace these cultures should they die before the end of the term of a patent issued hereon, and its responsibility to notify the ATCC of the issuance of such a patent, at which time the deposits will be made available to the public. Until that time the deposits will be made available to the Commissioner of Patents under the terms of 37 CFR Section 1.14 and 35 USC Section 112.

Other embodiments are within the following claims. For example, derivatives of vectors pKB663, pKB712, and pKB750 may be used as expression vectors; or derivatives of pKB766 may be used as a precursor to an expression vector into which a suitable foreign promoter is inserted. By the term derivative I mean naturally occurring or engineered variations of the vector that conserve the desired functions.

I claim:

1. An expression vector for transforming a host bacterial cell and producing phenylalanine, said vector comprising:
   (a) a pheA gene, said gene being free from naturally associated transcriptional regulatory sequences reducing transcription responsive to phenylalanine; and
   (b) a promoter positioned to express said pheA gene, said promoter being heterologous to said gene and substantially insensitive to the presence of phenylalanine.

2. The expression vector of claim 1 wherein said host bacterial cell is a member of the genus *Esherichia coli.*

3. The expression vector of claim 1 wherein said vector is selected from the group consisting of pKB712 (ATCC 39856) and pKB750 (ATCC 39857).

4. The expression vector of claim 1 further comprising an aroF gene, positioned in an operon for expression from said promoter.

5. The expression vector of claim 1 wherein said promoter is the lac promoter.

6. The expression vector of claim 1 wherein said promoter is selected from the group consisting of the promoter of M13 phage gene II, the tet promoter of pBR322, and the aroF promoter.

7. The expression vector of claim 1 wherein said vector is pKB663 (ATCC 39462).

8. A bacterial cell transformed with the expression vector of claim 3, claim 4, or claim 6.

9. A bacterial cell transformed with the vector of any one of claims 1, 2, 5, or 7.

10. A method of making phenylalanine comprising culturing the cell of claim 9 or claim 8 in a culture medium and recovering said phenylalanine from said medium.

* * * * *

UNITED STATES PATENT AND TRADEMARK OFFICE
CERTIFICATE OF CORRECTION

PATENT NO. : 4,839,286

DATED : June 13, 1989

INVENTOR(S) : Keith C. Backman

It is certified that error appears in the above-identified patent and that said Letters Patent is hereby corrected as shown below:

Column 7, line 42, "KB285/pKB663 or KB285/pKB663" should be --KB280/pKB663 or KB285/pKB663--.

Signed and Sealed this

Eleventh Day of June, 1991

Attest:

HARRY F. MANBECK, JR.

Attesting Officer

Commissioner of Patents and Trademarks